US007927558B2

(12) United States Patent
Kirollos et al.

(10) Patent No.: US 7,927,558 B2
(45) Date of Patent: Apr. 19, 2011

(54) SYSTEM AND APPARATUS FOR DETECTING BREACH OF EXPOSURE PROTECTION EQUIPMENT

(75) Inventors: Kirollos S. Kirollos, Virginia Beach, VA (US); Gueorgui M. Mihaylov, Virginia Beach, VA (US); Bryan I. Truex, Belleair Beach, FL (US)

(73) Assignee: Microteq, LLC, Virginia Beach, VA (US)

( * ) Notice: Subject to any disclaimer, the term of this patent is extended or adjusted under 35 U.S.C. 154(b) by 1897 days.

(21) Appl. No.: 10/782,494

(22) Filed: Feb. 18, 2004

(65) Prior Publication Data
US 2004/0223876 A1 Nov. 11, 2004

Related U.S. Application Data

(60) Provisional application No. 60/448,437, filed on Feb. 18, 2003.

(51) Int. Cl.
*G01N 33/00* (2006.01)

(52) U.S. Cl. ....... 422/400; 422/426; 422/430; 422/68.1; 436/1; 436/3; 436/164; 2/457

(58) Field of Classification Search .................. 436/1, 3, 436/164; 422/50, 400, 426, 430, 68.1; 2/457
See application file for complete search history.

(56) References Cited

U.S. PATENT DOCUMENTS

| 5,734,323 | A | * | 3/1998 | Hermes et al. | 340/540 |
| 5,976,881 | A | * | 11/1999 | Klingner | 436/3 |
| 7,514,039 | B2 | * | 4/2009 | Loomis et al. | 422/62 |
| 2002/0011934 | A1 | * | 1/2002 | Cacioli et al. | 340/604 |
| 2004/0141879 | A1 | * | 7/2004 | Loomis et al. | 422/58 |

* cited by examiner

*Primary Examiner* — Lyle A Alexander
(74) *Attorney, Agent, or Firm* — Troutman Sanders, LLP; Bernard G. Pike

(57) ABSTRACT

A method, system, and apparatus are provided for use with exposure protection systems or equipment such as respiratory protection devices. One system is provided for detecting a breach of an exposure protection device by an amount of a target substance. The system includes an exposure protection device that isolates a protected environment from an external environment potentially including a target substance. The device includes a protective covering that includes a substantially transparent window. The system also includes a detector or detector element for indicating the presence of the target substance. Such a detector is capable of producing a visually observable indication upon detection of the level of target substance.

22 Claims, 8 Drawing Sheets

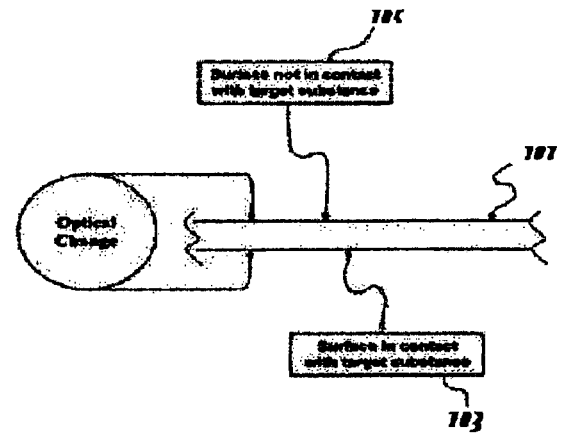
FIG. 1
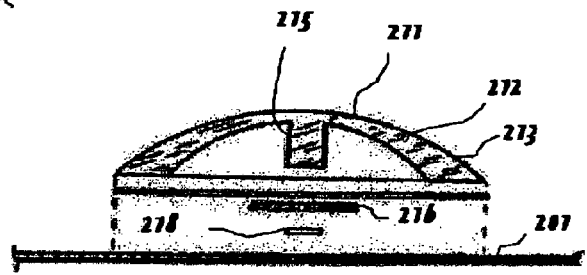
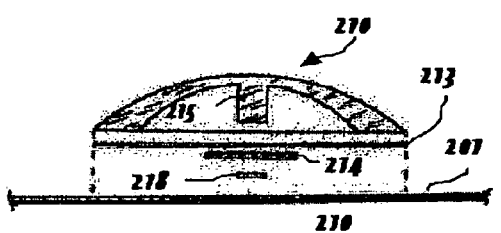
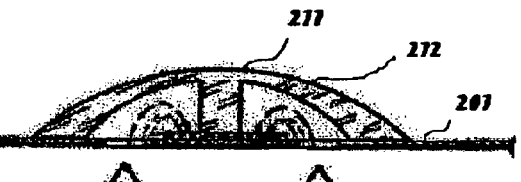
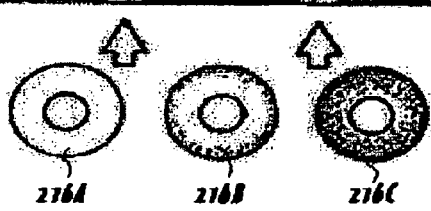
FIG. 2-A
FIG. 2-B
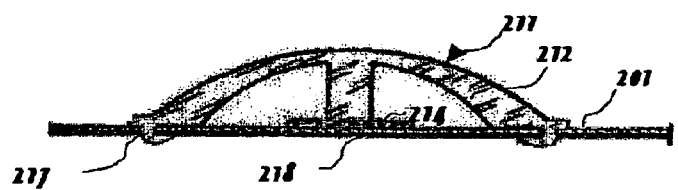
FIG. 2-C

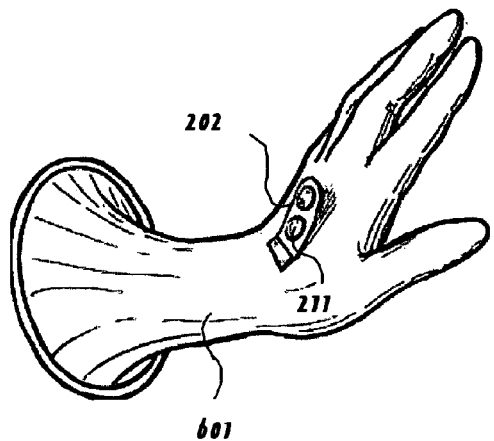
FIG. 3-A
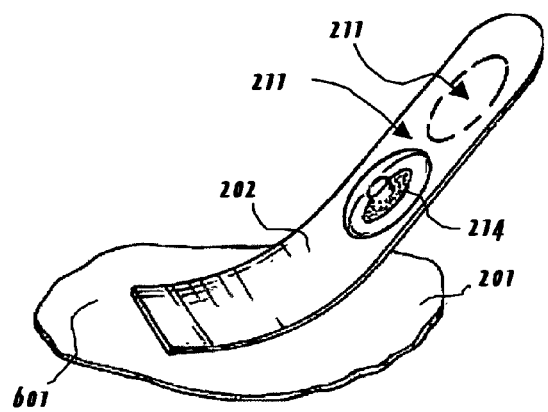
FIG. 3-B
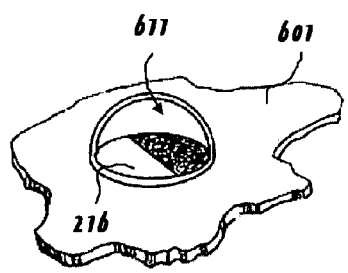
FIG. 3-E
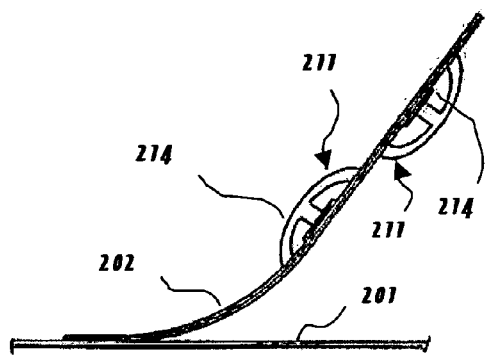
FIG. 3-C
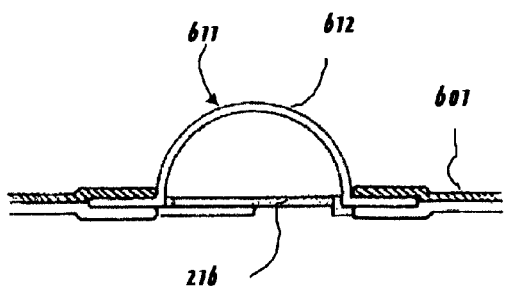
FIG. 3-F
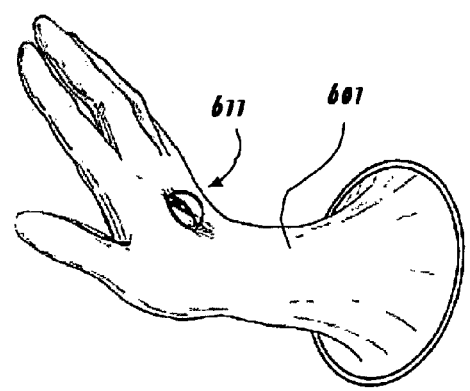
FIG. 3-D

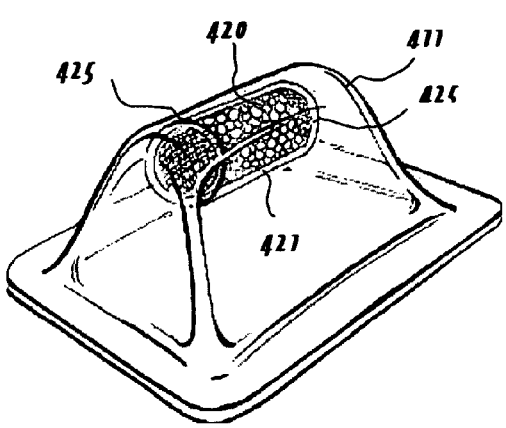
FIG. 4-A
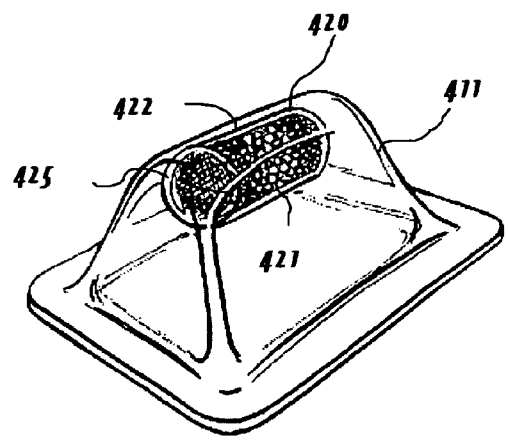
FIG. 4-B
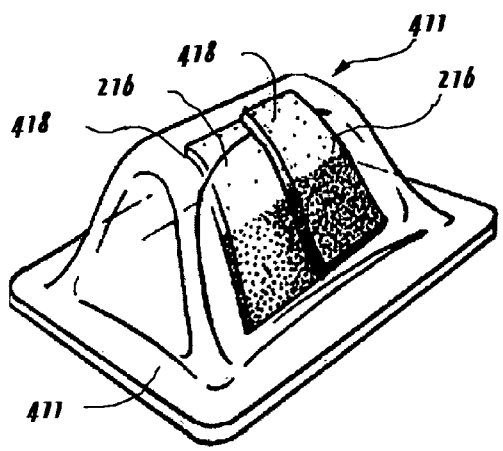
FIG. 4-C
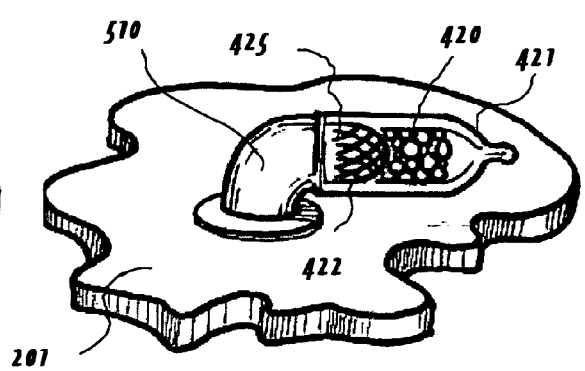
FIG. 5-A
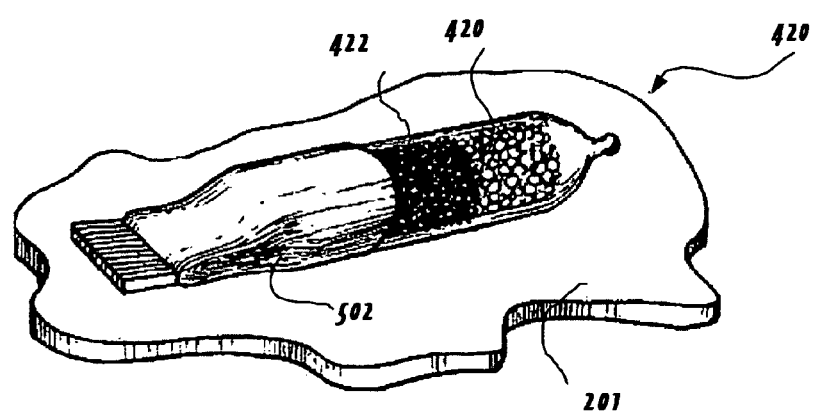
FIG. 5-B

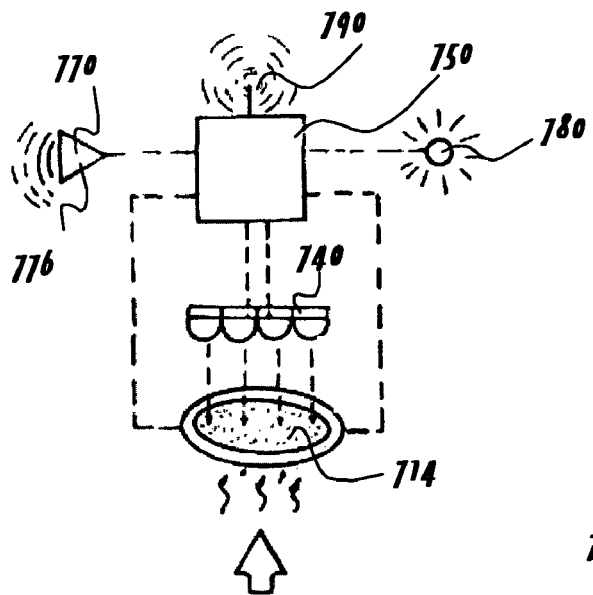
*FIG. 6-A*
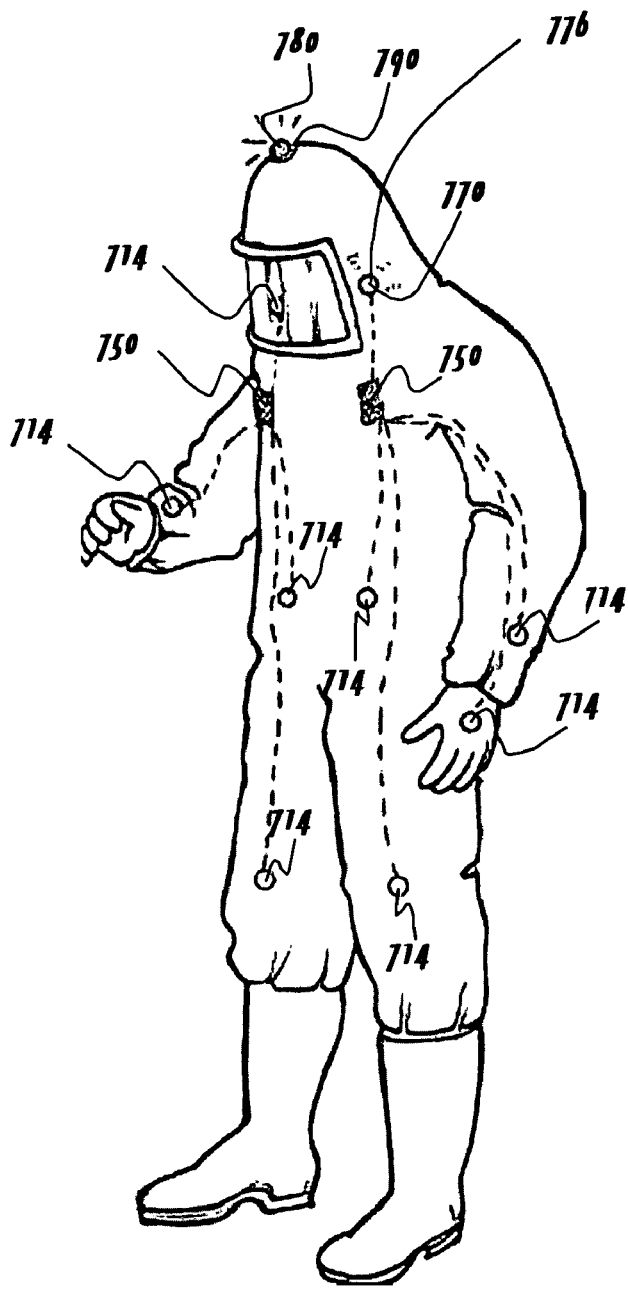
*FIG. 6-B*

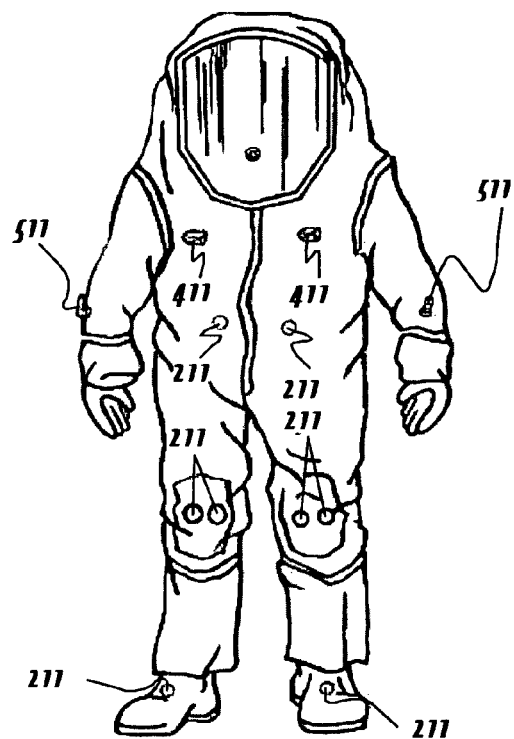
*FIG. 7-A*
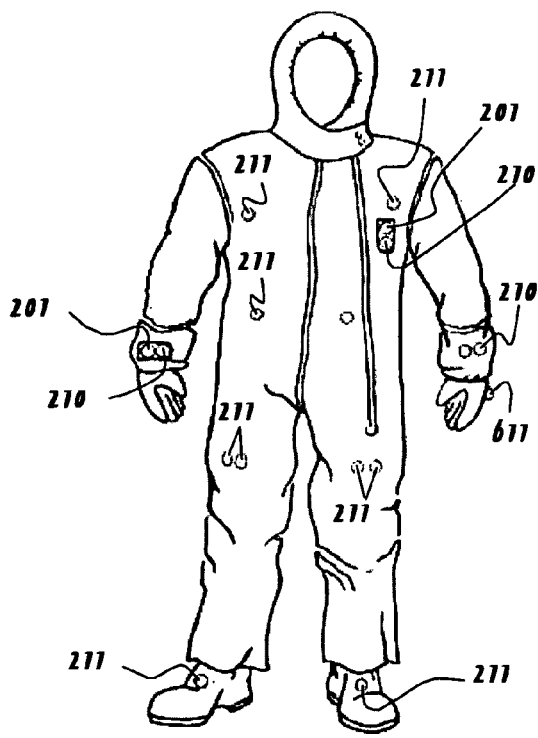
*FIG. 7-B*
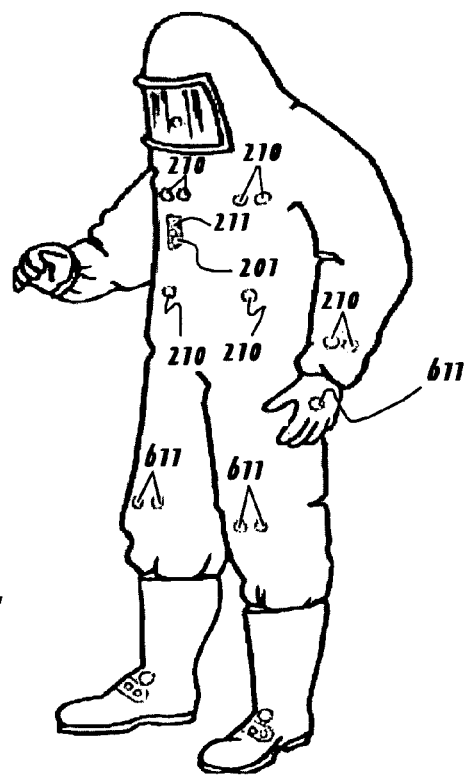
*FIG. 7-C*

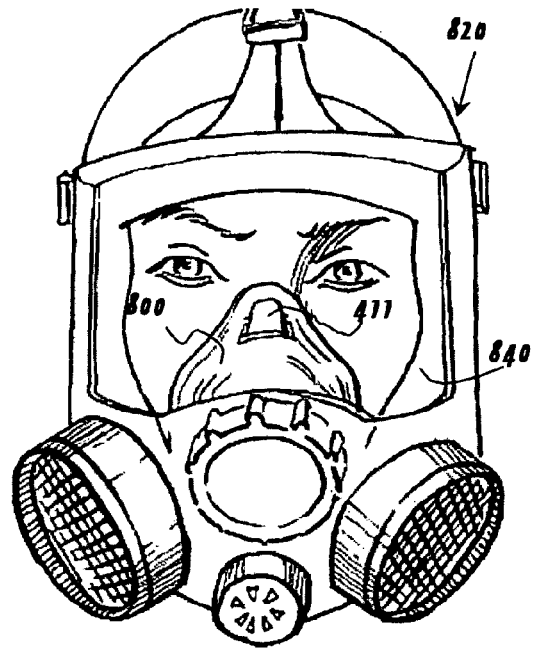
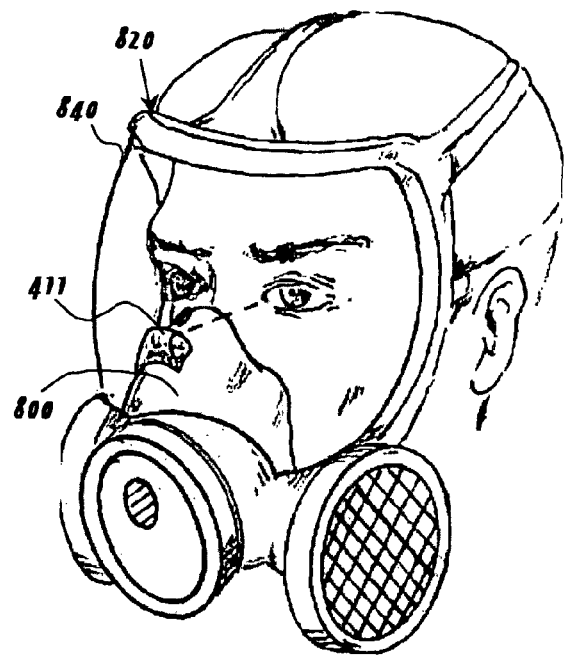
*FIG. 9-A*  *FIG. 9-B*
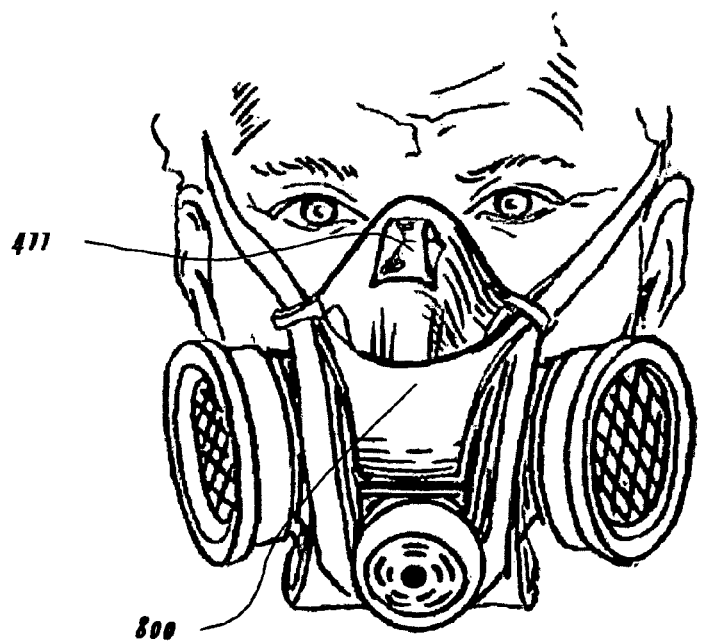
*FIG. 9-C*

SYSTEM AND APPARATUS FOR DETECTING BREACH OF EXPOSURE PROTECTION EQUIPMENT

The present application claims the benefit of the filing date of U.S. Provisional Application Ser. No. 60/448,437 filed on Feb. 18, 2003 (now pending) (which is hereby incorporated by reference for all purposes and made a part of the present disclosure).

BACKGROUND OF THE INVENTION

The present invention relates generally to a system, apparatus, and/or method for protecting against exposure to harmful environments. In this regard, the present invention relates generally to exposure protection devices. More particularly, the present invention relates to such a system, apparatus, and/or method for detecting a breach of exposure protection devices such as respiratory protection equipment, gloves, shoes, hoods, boots and the like (hereinafter referred to collectively as "exposure protection equipment").

The present invention is directed to exposure protection equipment that guard or isolate an internal protected environment from an external environment that may contain harmful fluids, materials, particulates, and other substances ("harmful environment"). Applicants recognizer that, as with most safety equipments, exposure protection equipment are not necessarily failsafe and can, under certain circumstance, fail to provide absolute protection from the target harmful environment. A breach of the protected internal environment may be initiated in a number of ways, resulting in possible exposure to the harmful environment. A breach may result from repeated or extensive exposure of the protective clothing to the target substance and/or breakthrough of the target substance through the materials of the exposure protection equipment. The breach may result from a manufacturing defect and/or damage during use causing or manifesting in a seal failure or crack, tear, punch or other deformation of the materials of the exposure protection equipment. The exposure, or more specifically penetration of the fluids into the protected environment, may be slow or fast There are prior devices and methods for detecting such a breach of exposure protection equipment. U.S. Pat. Nos. 5,976,881 and 5,376,554 both teach a means or method of detecting and/or indicating a breakthrough of a protective gloves (i.e., a breach of the protective glove). The described methods require, however, removal or unzipping of the protective equipment to observe or monitor the detecting means or indicator and confirm whether a breach has occurred. In effect, the described methods require the user to possibly expose the intended protected internal environment in order to use the detecting means or indicator. The user is potentially exposed to an external harmful environment without necessarily knowing that he or she has been exposed. Unless the user frequently leaves the hazardous environment to remove the protective equipment and check the results, the user will not know the status of the detecting means or indicator.

U.S. Pat. No. 5,297,544 describes another detecting or indicating device for use with respirators. The described device is used specifically to monitor and indicate the presence of pollutants in the respirator. As with the previously described detecting or indicating mean, the construction of this device does not allow the user to use the device and readily confirm the presence of the pollutants. To do so, the user has to dismantle the device or employ an electronic reader in conjunction with the detecting sensor.

BRIEF SUMMARY OF THE INVENTION

Accordingly, it is one of multiple objectives of the present invention to provide a new and improved method, apparatus, and system for detecting or predicting a breach of exposure protection equipment (including, the properties of the "protective equipment"). In some embodiments of the invention, an objective is to provide such a method, system or apparatus for detecting a breach before the "actual breach" occurs and, alternatively, predicting the amount of time remaining at the current environmental conditions and concentrations of the target substance before the "protective equipment" fails. Another objective of the present invention is to provide a qualitative and/or quantitative means for determining and/or predicting the breach of properties of "protective equipment" before "actual breach" occurs. Yet another objective of the present invention is to provide the user of "protective equipment" with a means of observing the performance of the "protective equipment" while in use.

In one aspect of the present invention, a system is provided for detecting a breach of an exposure protection device by an amount of a target substance. The system includes an exposure protection device that isolates a protected environment from an external environment potentially including a target substance. The device includes a protective covering that includes a substantially transparent window. The system also includes a detector or detector element for indicating the presence of the target substance. Such a detector is capable of producing a visually observable indication upon detection of the level of target substance. Moreover, the detector is positioned within the protective environment such that the observable indication (e.g., visually observable) is observable from the external environment.

BRIEF DESCRIPTION OF THE DRAWINGS

FIG. 1 is a simplified schematic of a breach detector subsystem or system, according to the present invention;

FIG. 2A is a cross sectional view and diagram of an alternative breach detector subsystem, according to the invention;

FIG. 2B is a cross sectional view and diagram of an alternative breach detector subsystem, according to the invention;

FIG. 2C is a cross sectional view and diagram of yet another alternative breach detector subsystem, according to the invention;

FIG. 3A is an illustration of a protective exposure protection device incorporating a breach detector system, according to the invention;

FIG. 3B is a detailed view of the breach detector system in FIG. 3A;

FIG. 3C is a vertical cross sectional view of the breach detector system in FIG. 3B;

FIG. 3D is an illustration of an exposure protection system equipment incorporating an alternative breach detector system according to the invention;

FIG. 3E is a detailed view of an alternative breach detector system for use with the exposure protection device of 3A;

FIG. 3F is a cross sectional view of the breach detector system of FIG. 3E;

FIG. 4A is an illustration of an alternative breach detector subsystem according to the invention;

FIG. 4B is an illustration of an alternative breach detector subsystem, according to the invention;

FIG. 4C is yet another alternative breach detector subsystem according to the invention;

FIG. 5A is yet another alternative breach detector subsystem according to the invention;

FIG. 5B is yet another alternative breach detector subsystem according to the invention;

FIG. 6A is a simplified schematic of a system for detecting breach of an exposure protection equipment, according to the invention;

FIG. 6B is an illustration of an exposure protection equipment, incorporating a breach detector system according to the invention;

FIGS. 7A-7C are illustrations of alternative exposure protection equipment, incorporating breach detector systems, according to the invention;

FIGS. 9A and 9B are illustrations of full face mask exposure protection equipment, incorporating a breach detector system, according to the invention;

FIG. 9C is a respirator half mask exposure protection equipment, incorporating a breach detector system, according to the invention.

REFERENCE NUMERALS

Figure 8:
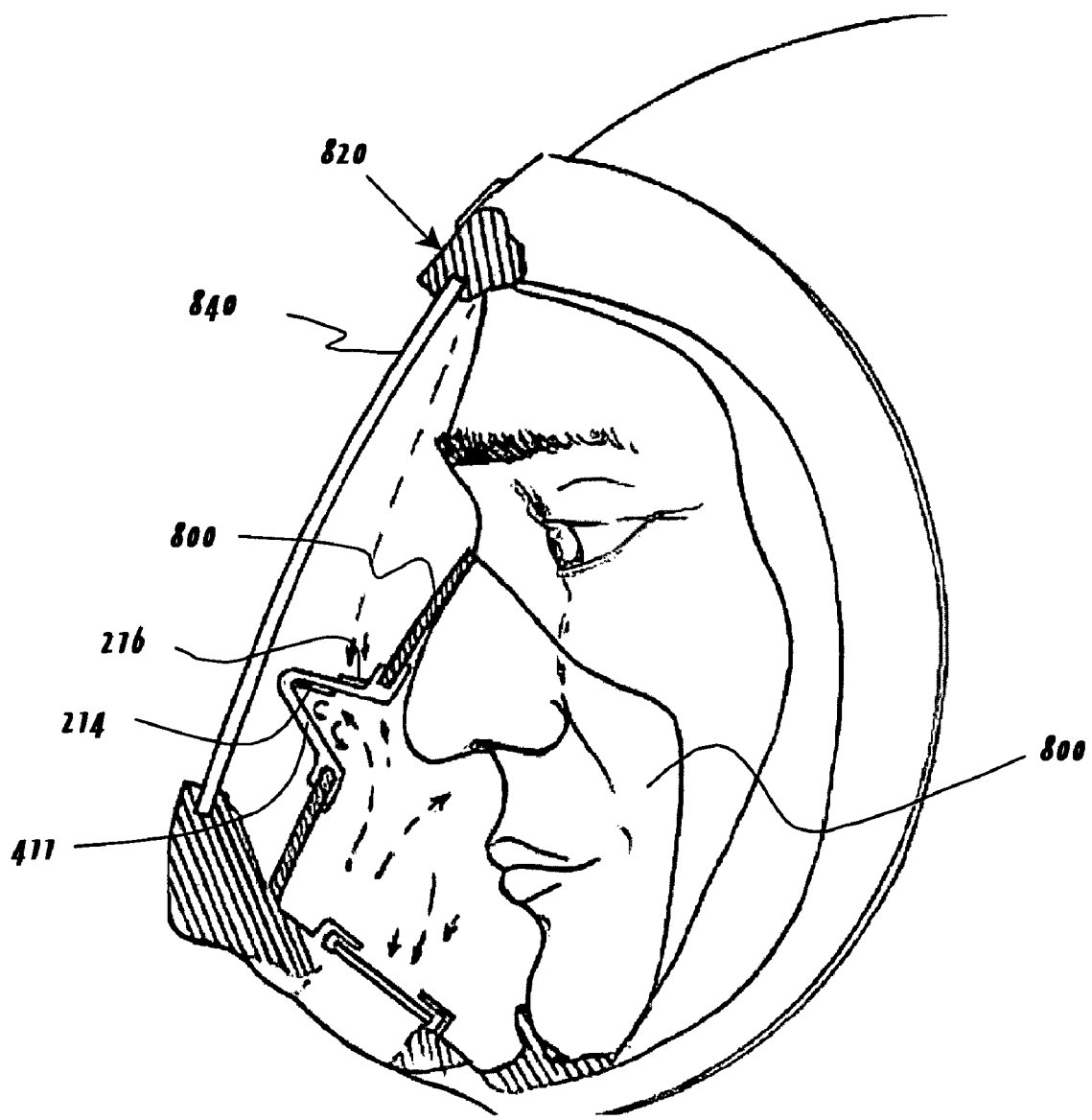
FIG. 8 is a side view of a full face mask exposure protection equipment, incorporating a breach detector system according to the invention.
Figure 10:
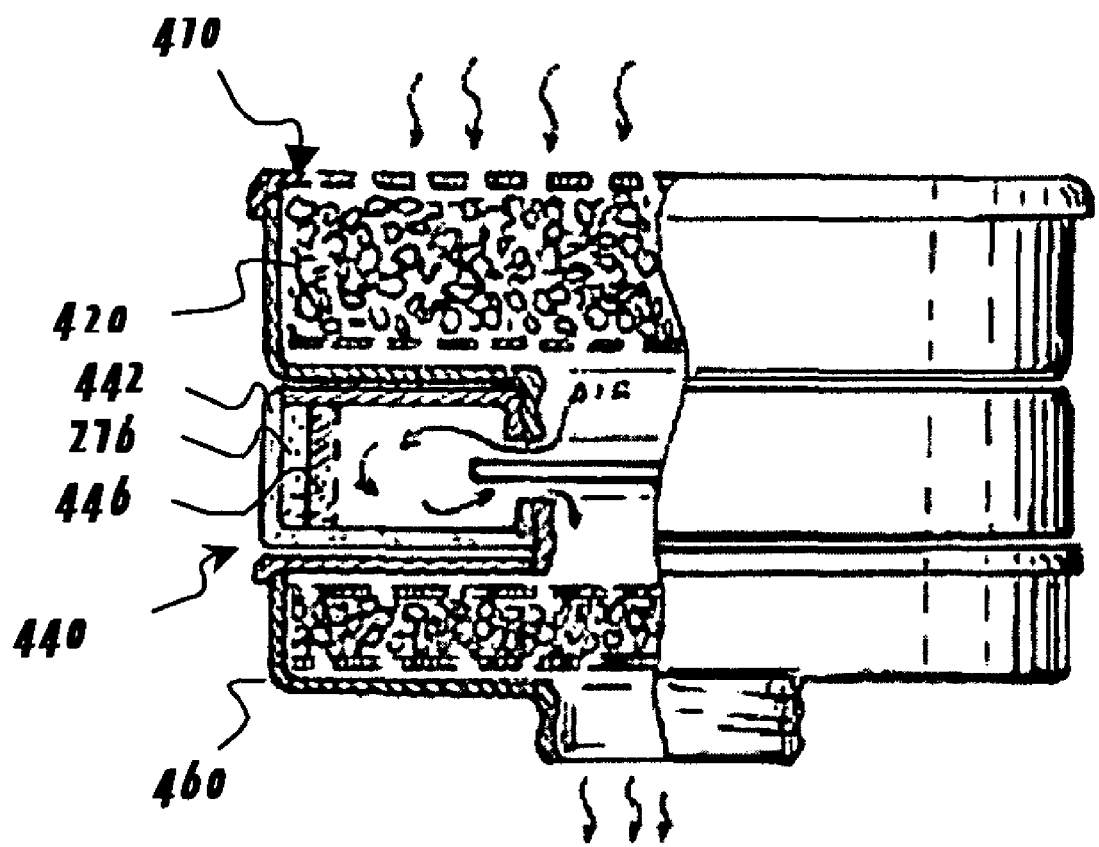
FIG. 10 is a side view and cut out view, of a cartridge device, incorporating a breach detector system, according to the invention.

201 Mono or multilayer material used for protective gear (clothing)
202 Mono or multilayer material same as the one for the protective gear used as attachment patch for monitoring permeation and material breakthrough.
210 Enclosure for monitoring permeation and breakthrough of protective material
211 Enclosure for monitoring hazardous concentration in the confined by safety equipment space
212 Cover lenses of the enclosures 210 and 211
213 Adhesive layer sealing enclosure to the material
214 Sensitive materials changing its optical properties upon exposure to chemical or biological substance having at least one active side exposed to substance
216 Sensitive materials changing its optical properties upon exposure to chemical or biological substance and having two active sides
217 Pins for riveting—optional portion of the lenses
218 Chemical inert mask between the sensitive material and monitored material
411 Grommet-type prismatic lenses containing sensitive materials
418 Transparent thin layer impermeable mask over part of sensitive materials 214 or 216
420 Length-of-stain-type enclosure of detector/indicator
421 Sensitive solid material/filler into length-of-stain-type device unchanged
422 Reacted and optically changed sensitive material 421
425 Permeable retaining cups into length-of-stain enclosures
502 Sleeve-type camera made from monitored material and hermetically connected to length-of-stain enclosure
510 Chemically inert connector between monitored confined space and length-of-stain enclosure
601 Glove made from protective material
611 Enclosure for detector/indicator of protective gloves
612 Lens of enclosure for glove monitoring
714 Piezo-optic sensor
740 Irradiating source
750 Processor
770 Audible signal
780 Visual signal
790 Remote transmitting member
800 Half-mask for respiratory protection or inner half mask into full-mask
820 Full-face mask for eye and respiratory protection
840 Lens of the full-mask

DETAILED DESCRIPTION OF THE INVENTION

FIGS. 1-10 depict various systems and/or apparatus for detecting a breach of an exposure protection detection equipment or device, or alternatively, breach of the protected environment, by a target substance(s) present in the target harmful environment. Each of the depicted systems or apparatus embodies one or more aspects of the present invention. Each of these systems include or is associated with an exposure protective equipment, as previously described, defines an internal protected environment so as isolate it from an external harmful environment (possibly including the target substance). The protected internal environment is generally situated between the protective equipment, or components thereof, and the user or part of the user's body. It should be noted that, in various embodiments, the protected internal environment is in communication with the respiratory system of the user. In further embodiments, the protected internal environment is communication with other parts of the user's body. In one aspect of the invention, the inventive system employs a breach detector subsystem including a detector element, such as a colorimetric change indicator or piezoelement and reagent combination. The detector element is situated in, in engagement with or communicates with the protected internal environment. It should be noted that, as used herein, the term "protected internal environment" may include the space between the exposure protection equipment and the user, all or parts (e.g., hand, head, respiratory system, etc.) of the user, and all or part of the internal portions of the exposure protection equipment.

In preferred methods, the detector element is used to monitor the internal protected environment and possibly detect breach thereof by target substance(s) from the external harmful environment and then communicate the breach or otherwise provide an observable indication of the breach. For example, in certain embodiments, the detector element is a calorimetric change indicator located within the internal protected environment and provides a visually observable indication to the user or other person upon detection of a target substance in the internal protected environment. The visual observation may be made, from the outside, through a transparent window in the protective equipment.

Multiple exemplary embodiments are described herein. A general objective of at least several of these embodiments is to provide the user, as well as authorized personnel with an immediate warning by one or more "in situ" visual, audible, tactile and/or remote alert signals. Other embodiments provide a method, system, and apparatus for use with protection systems such as respiratory protection devices, and more particularly, such a method, system, and apparatus utilizing a secondary system breach detector and indicator (wherein, the first or primary detector may be the user).

Alternative embodiments described herein provide means and methods for the detection of leaks of the "protective equipment" due to bad seals, cracks, tears, punched or pierced material or other breaches of the protective barrier of the protective equipment resulting in a slow or fast increase of the "target substance(s)" in the space confined by the protective equipment ("internal protected environment"). Alternative system also provide means for the detection of a breakthrough in a respiratory facemask or the components of the respirator system, including breakthrough of the filters, the mask, the filter housing and/or air supplying system leading to an increase of the "target substances" confined by the "protective equipment. Alternative embodiments further provide a means for detection and prediction of breakthrough of the "protective equipment" material used in the construction of body suits, shoes, boots, hoods, gloves, respiratory facemasks that may lead to an increase of the "hazardous fluids" confined by the "protective equipment."

One method of detection, according to the invention present invention, involves three stages;

(1) exposing a sensor that in the presence of the analyte in the space confined by the "protective equipment" (protective clothing) undergoes an identifiable and or qualitative and or quantifiable change such as a visual, structural, electrical, temperature, mass, mechanical deflection, optical absorption, optical emission, pressure, optical reflectivity or absorption and/or adsorption change;

(2) exposing a similar type of sensor to the environment external to the protective equipment; and (3) exposing a similar type of sensor in a limited volume confined space, hermetically sealed from the environment external to the space confined by the protective equipment such as a small chamber or cell, which has one analyte resistant wall formed by one or more layers of the barrier material used for the protective equipment and another wall from analyte inert material transparent for visual or, other observation. The exposed sensor can be examined, interrogated, read by direct observation and/or by other physical means for characterization of structural, piezoelectric or pyroelectric, electrical resistance, luminescence, optical absorption, optical reflectivity, optical emission, mass, impedance, temperature, and complex electric permittivity changes.

In a further aspect of the invention, the method employs an adhesive or user attachable analyte (chemical, biological, and/or other) detector to indicate a breach of the respiratory system. The detector maybe placed on the user in the space isolated from the potentially dangerous environment, thereby serving as the secondary means (in addition to the user) of detecting passage of any of the "hazardous fluids" into the protected space confined by the protective equipment.

In another aspect of the invention, a method for testing the integrity (e.g., fit, quantitative fit and or qualitative fit) of the respiratory protection system utilizes a secondary analyte, chemical, biological and/or other detector and qualitative or quantitative fit of "protective equipment" utilizing a secondary analyte, chemical, biological and/or other detector. Preferably, the secondary detector has the capability of producing an observable and/or qualitative and/or quantitative indication upon exposure of the sensor to a predetermined level of the target analyte hazardous fluids, aerosols and/or particulates.

In another aspect of the invention, a method and device is provided for detecting and indicating the end of service life of the protective equipment before the breach of properties of the protective equipment occurs and the extension of the manufacturers specified respirator service life. In yet another aspect of the invention, a method and device is provided for detecting and indicating the presence of chemical warfare nerve agents for the purpose of determining if it is all clear or safe to discontinue the use of a respirator.

FIG. 1 depicts, in a simplified schematic, one embodiment of a detector element for detecting breach of exposure protection equipment or, alternatively, breach of the protected environment as utilized in the present inventive system, apparatus, and method. In this embodiment, the detector element is provided in the form of a colorimetric or a fluorescent device 101, e.g., in the form of a badge, patch, sensor or length of stain tube (sometimes referred to herein as a "colorimetric change indicator" or simply "change indicator"). The colorimetric device 101 has the capability of undergoing an observable change (i.e., color change) in the presence of a target substance (in the harmful environment). Preferably, the calorimetric patch or sensor or length of stain tube provides an optical change that is visible to the human eye or visible under ultraviolet light, or visible with infrared imaging technology. The terms "optic change" or "color change," in this respect, includes a change from a non-fluorescent state to a fluorescent state or from a fluorescent state to a non-fluorescent state or illumination of a change when exposed to ultraviolet light. In various applications of the invention, the change indicator may indicate the presence of chemicals, biological material, hazardous fluids, toxins, contaminates, or a temperature variation. Typical target substances include certain chemicals, protein, spore, dust, biological material, metal, toxins from fungus plant and organisms and biological warfare agents and chemical warfare agents.

The colorimetric device 101 of FIG. 1 has a contact surface 103 and a non-contact surface 105. The contact surface 103 is adapted for contacting the target substance, wherein the non-contact surface 105 is typically positioned away from the target substance. Both surfaces are capable, however, of indicating an observable color change, upon detection of the target substance. This type of multi-surface calorimetric device 101 is particularly suited in an application wherein the contact surface 105 is not readily visually observable or, alternatively, wherein the non-contact surface is not positioned for ready access to and contact with the protected internal environment. In some applications, for example, the contact surface 103 may be in direct contact with the user's skin. Other suitable applications are further discussed below or will become apparent from a reading of the present Description and/or viewing of the accompanying Drawings.

In one alternative embodiment, the detector element or change indicator is provided in the form of a piezoelectric film and reagent combination that changes or reacts in the presence of a target substance when interrogated by light energy. This interrogation generates an electrical signal that is proportional to the concentration of the target substance. The electrical signal may then be interpreted by operation of an algorithm. The schematic of FIG. 6A illustrates such a charge indicator system 700 employing a piezoelectric film transducer 714, irradiating energy source 740, and a processor 750 for processing or operating the algorithm.

Piezo electric technology that is particularly adapted for use with the inventive methods and apparatus is discussed in PCT Application US02/23309 filed Jul. 18, 2002 (filed at least on behalf of one inventor common to the present application) and. Also discussing relevant Piezo electric technology is U.S. Pat. No. 5,622,868 (issued to Clarke on Apr. 22, 1997). Both of the above patent documents are hereby incorporated by reference for all purposes and should be regarded as part of the present disclosure.

By operating a digital signal, the change indicator can be programmed to provide a quantitative measure of the target substance or a qualitative indication that the target substance is present or a semi-quantitative indication that a minimum amount of the target substance is present. The piezoelectric film and reagent device may also trigger audible, visual, and vibrating alarms. Upon detection of a hazard, the processor generates signals to audible signaling device 770, visual (light) signal 780, tactile signal (vibrating) and translates the warning to a centralized remote location, via transmitting member 790. The device can indicate the presence or quantity of one or more target substances (e.g., simultaneously) including one or more analytes and temperature and or humidity. The piezoelectric change indicator may also indicate the temperature and/or humidity of canister, cartridge or filter incorporated with the device or indicate the temperature or humidity of the target substances in the filter.

With the use of the inventive color change indicator and pyroelectric or piezoelectric element combination, a membrane may be disposed between the reagent material and the filter material, or target substance. Use of transparent opaque or non-transparent hydrophobic, or permeation selective membrane over the reagent used on, or used adjacent to a pyroelectric or piezoelectric element. This provides protection of reagent from substances that may degrade the reagent as well as providing protection from liquid contracting the reagent including water or water vapor and/or providing filtering of substances allowing same to be exposed to the reagent and preventing others from being exposed to the reagent such as poisons or cross interferences. This embodiment does not require that the color change of the change indicator be visible to the human eye.

Thus, the observable change of the calorimetric, fluorescent or length-of-stain device, patch or sensor may be qualitative, semi-qualitative, or quantitative, and may be determined manually or automatically. Typically, the extent of the color change is proportional to the concentration or amount of the target substance. This can be determined quantitatively by comparing the intensity of the color change to a chart of color changes or to a chart of different intensities indicating different concentrations. The result can also be determined automatically by measuring the intensity of reflective light which is of the concentration of the target substance and density of optical change in the indicator. The change indicator color change can be automatic and quantitative by measuring as reflective light with the concentration or amount of the target substance proportional to the darkness of the color change as measured with reflective light. This is identical to the method used to determine concentration with paper tapes.

FIGS. 4 and 5 illustrate alternative embodiments of the inventive breach detector subsystem, each of which employs a length-of-stain type of detector or change indicator. In the breach detector system of FIGS. 4A and 4B, the length-of-stain detector is provided in a transparent tube that is open at both ends, thereby fluidly communicating with internal protected environment. In the system of FIGS. 4C, the length-of-stain detector is provided in the form of relatively flat strips. Length-of-stain type detectors suitable (perhaps, with some structural modification) for use with various embodiments of the invention are generally known in the art. In one set of embodiments, the change indicator is constructed as a direct reading detector tube 201 that is open at both ends 201a, or alternatively, open at one end 201b (see FIG. 2). Such a device functions similarly to a dosimeter, and works by way of diffusion. The change indicators 201 are placed inside the container 203 and are observable through the windows 205.

In one aspect of the invention, the inventive system or method incorporates a calorimetric badge or patch capable of changing color in the presence of a target substance (e.g., chemical proteins, spores, dust, biological materials, metals, toxins from fungus plants, plants and organisms, biological warfare agents, and chemical warfare agents). Generally, the patch indicates a color change on one surface when that surface is contacted with the target substance. The same patch preferably indicates an observable color change or indication on the opposite surface that is not in contact with the target substance. In these applications, the color change typically will be one visible to the human eye, but may, in the alternative, be one visible under ultraviolet light or with infrared imaging technology. In any event, the color change includes an observable indication such as a change from non-fluorescent to fluorescent states or from fluorescent to a non-fluorescent state or when exposed to ultraviolet light.

In a first application of the present invention, a colorimetric patch is used in conjunction with or incorporated with environmental filters, particularly those used to remove, absorb, or alter the target substance, such as those used in respiratory protection equipment. In these applications, the target substance may be a type of poison, a toxin, a chemical, an organism or some other contaminant or interferent. Further, the filter may be adapted for liquids, gas, dust vapors, or particles, or some other substance.

In such an application, the colorimetric patch is preferably housed in a clear container (as described previously), which allows the back of the color change indicator to be observed from the exterior of the filter container.

In another aspect of the present invention, a colorimetric device, patch or sensor or length-of-stain device is used in conjunction with or incorporated with environmental filters such as those used in respiratory protection equipment and/or transformers, particularly those used to remove, absorb, or alter the target substance. In these applications, the target substance may be a type of poison, chemical, protein, a microorganism, spore, dust, metal, biological warfare agent, chemical warfare agent, toxin, or biological material or some other contaminant or interferent. Further, the filter may be adapted for liquids, gases, dust, vapors, aerosols or particles, or some other substance. In such an application, the calorimetric patch is preferably housed in a clear container. This allows the back of the color change indicator to be observed from the exterior of the filter container.

Preferably, the change indicator is placed inside the container before the filter material is added. The filter material is placed in the container in direct contact with the color change reagent to achieve greater sensitivity and speed of response. The change indicator may be separated from the filter material or it may be placed in contact with the filter material. The material used in the filter either absorbs the target substance, blocks the target substance from passing through the filter. The material used in the transformer converts the target substance to another substance that is not considered harmful or detectable by the calorimetric, fluorescent, length-of-stain device, patch or sensor or converts the target substance to a substance that can be detected by the change indicator depending upon the application and the target substance.

FIGS. 2A-2C illustrates embodiment of breach detector subsystem for use with an exposure protection system. As will become apparent from the present Description, the subsystems of FIGS. 2A-2C are particularly suited for use with exposure protection equipment such as gloves, boots, hoods, and suits. The breach detector subsystems preferably employ a detector element or change indicator such as a calorimetric patch disposed within the internal protected environment and generally under an enclosure 211. The enclosure 211 includes or provides a substantially transparent window or lens 212 through which a detector element or change indicator 216 (such as those previously described and illustrated _____).

The lens 212 is hermetically sealed to a material surface or component 201 of the protective equipment, for example, by adhesive or sealant 213. Openings 201 in the material surface 201 and under the lens 212 allow for free diffusion from the confined protected space (between the protective equipment and the user) to the change indicator 216. Preferably, a stem 215 is provided that extends downwardly from the lens 212 and blocks a middle portion of change indicator 216 from exposure.

Each of FIGS. 216A through 216C depicts the change indictor at different stages of exposure. The change indicator 216 preferably changes color gradually as shown from 216A to 216C. This color change is easily observable from the external environment through lens 212. Because the middle portion of the change indicator 216 is not exposed, it maintains its easily distinguished initial color, thereby providing a readily observed contrast to the exposed portions of the change indicator. Accordingly, the breach detector subsystem of FIG. 2A serves as a leak detector, breakthrough indicator and monitor of the defined internal protected environment.

FIG. 2B provides an alternative embodiment of the breach detector subsystem having a construction similar to that for the subsystem of FIG. 2A. In this embodiment, the isolated space immediately under the lens 212 is isolated (i.e., openings 216A are not provide in the material surface) from the protected internal environment as well as the external harmful environment. The target substance can penetrate and enter the isolated space (i.e., form the external harmful environment) only by diffusion through the protective material 201. The surface of the enclosure 212 is preferably made substantially larger than the surface of the change indicator 214 so that even a small amount of the target substance permeating through the material can be detected. Accordingly, the breach detector subsystem is able to detect the end of service life of the material of the protective equipment before the permeation flow reaches a predetermined value. To serve as such a detector, a patch of material identical to the material construction of the protective equipment may be mounted Preferably, the patch material is selected such that it has 70% to 90% of the protecting capacity of the protective equipment material and is situated on the outer surface of the equipment.

The breach detector subsystem of FIG. 2C also has a construction similar to that of the subsystem of FIG. 2A. The enclosure 211 is equipped, however, with pins 217 that extend from the lens area 212. The pins 217, which may be provided continuously, are used to rivet the enclosure 211 to the material surface of the protective equipment.

FIGS. 3A through 3C depict breach detector subsystems that employ a patch of material such as that described in the subsystem of FIG. 2B. These detector systems further employ a detection element in the form of a color change indicator, which is visually observable through an enclosure having a transparent lens. In the Figures, the patch of material is mounted to safety gloves, or other parts of the protective equipment (see also FIGS. 7B and 7C). As explained with respect to the embodiment of FIG. 2B, the patch of material is selected so as to simulate the performance or integrity of the material of the protective equipment in the external harmful environment, and, more preferably, such that it indicates a possible future breach of the protective equipment (prior to actual breach and/or exposure).

Another variant of the above concept is depicted by FIG. 5B. The patch of material as used for the protective equipment 502 is hermetically sealed around the inlet of length-of-stain device 420. Upon permeation through the walls of the pouch 502 the hazardous materials reacts and discolor sensor material 421 to color changed 422. This embodiment is preferred one for solvents and other organic materials. An alternative to the device shown on FIG. 2-A are length-of stain embodiments shown on FIG. 4-A, 4-B and FIG. 5-A. In all of those embodiments there is direct connection between length-of stain device and protected environment; therefore they are considered detector/indicators for leaks and/or end of service life for the protective equipment.

Now referring to FIGS. 3-A to C, yet another embodiment of the invention incorporates the inventive change indicator in a protective equipment environment. One difference, however, is that the inventive protective equipment change indicator does not require automatic monitoring or measuring of the quantitative amount of the target substance with reflective light. Preferably, the protective equipment 601 is provided with a clear window 612 through which the color change indicator 214 and 216 are visible. The surface of the color change indicator is situated between the protective equipment and the body of the wearer, and such that the back of the color change indicator is visible from the surface of the protective equipment through the non-permeable clear, barrier or window. The change indicator may be used to indicate the presence of the target substance, the concentration of the target substance and the temperature and humidity in the protective equipment 601 as an indication of heat stress.

The color change indicator may be installed in the protective equipment by cutting and punching a hole through the surface of the protective equipment. The color change indicator is then mounted with the clear window in place, and then sealed to the protective equipment such that there is a permanent seal there between the clear window and the protective equipment, and with the same integrity as the remaining surface of the protective equipment. The color indicator may be riveted to the protective equipment with clear window facing the user and the rivet seal the indicator with the protective equipment with the same integrity as the remaining surface of the protective equipment. Alternatively, the protective equipment may be manufactured with a clear window and the color change indicator is mounted in the clear window later.

In yet another alternative embodiment, the color change indicator is removable or disposable with one or more predetermined uses. The change indicator may be disposable with each use, but another indicator may be added as a replacement and the protective equipment then worn again. In yet another variation, the color change indicator is incorporated into the protective equipment by adding a clear blister 612-above the surface of the protective equipment (see FIG. 3-D to F). In this way, the color change indicator does not rub or contact the operator's hand. The blister 612 (bubble window) also provides a convenient head space for monitoring.

The change indicator may also be a piezoelectric film with reagent. In this variation, the protective equipment need not be equipped with a window as described above. The reagent side of the film faces the wearer's hand and an LED is provided on the back side of the film. In these applications, fiber optic cable or light tube may be provided for delivering LED light to the film (so as to generate the signal).

In another aspect of the invention a transformer converts specific substance to another substance capable of being detected by the change indicator. The transformer can also be capable of localizing by absorption, adsorption and/or converting and/or blocking and/or trapping undesired substances such as poison and cross interferent substances from passing through and detected by the change indicator. The transformer can be chemical transformer or biological transformer.

In another aspect of the present invention, the transformer can be placed between the filter material and a market available sensor housed in the same container. The sensor can be Acoustic IR sensor, Biological sensor, Chemfet sensor, Colorimetric sensor, Conductive polymer sensor, Enzyme sensor, Fiber optic sensor, Photo ionization detector, Fluorescence detector, Immobilization of recombination bioluminescent bacterium sensor, Immunoassay sensor, Infrared coherent laser source sensor, Infrared sensor, Ionization sensor, Laser sensor, Metal Oxide sensor, Piezoelectric sensor, Pyroelectric sensor, Surface Acoustic Wave sensor, Solid State Semi-Conductor sensor, Thermal Conductivity sensor, Voltametric Electrocatalytic sensor or Wave Guide sensor.

An example of the function and properties of a chemical transformer is depicted by the colorimetric detection of Acetaldehyde. There is no available electrochemical sensor for Acetaldehyde. A transformer containing Hydroxylamine hydrochloride reacts with Acetaldehyde to generate HCl. An HCl electrochemical sensor can then be used to directly detect a concentration of HCl that is proportional to the concentration of Acetaldehyde.

Another example of the function and property of a transformer is the use of a molecular sieve of Zeolite or the use of Anhydrous calcium chloride to trap, localize, block the flow of, or absorb or adsorb water and/or water vapor such that the water or water vapor does not react with the change indicator's reagent or react with other sensors or degrade the change indicator or other sensor performance.

An example of chemical transformer; there is no available sensor for Acetaldehyde. A transformer contains $(NH_2OH)_3$·HCl reacts with Acetaldehyde to generate HCl. An HCl sensor which can be electrochemical sensor, mass sensor, catalytic sensor, thermal sensor, pyroelectric, chemfet sensor or optical sensor is used to detect HCl and therefore Acetaldehyde can be detected.

A transformer that traps water and/or water vapor and/or localizes water or water vapor by adsorption and/or absorption and/or converts water and/or water vapor to a substance that does not degrade and/or react with the reagent.

Preferably, the change indicator is constructed of an inert material. The carrier is preferably fibrous structure such as mesh-like, woven or non-woven textile-felt 214, 216 shown on FIG. 2, FIG. 3, and FIG. 4C. It may also be constructed of Teflon or paper. Further, the change indicator may be made of a silica or silicone. A membrane typically covers the reagent. In one application, the filter media is coded or impregnated with the reagent that absorbs, blocks, or reacts with the target substance. The color change is typically visible in both the face and the back of the color change indicator. The clear container allows the user or reflected light or other device to recognize when the color change occurs and the extent of the color change. In these applications, the change indicator indicates:

(1) The target substance has reached a certain point in the filter indicating either the amount of time or the percentage of filter remaining, before the failure of the protective equipment or that a filter change is required;
(2) The percentage of the filter that remains unused;
(3) The color change indicator advises the user when it is time to change the filter to ensure that no poisons, chemicals, proteins, spores, dust, metals, biological warfare agent, chemical warfare agent, contaminants, interference, toxins, or biological material passes through the filter; and
(4) The color change indicator may be a series of spots that changes as the target substance moves through the filter.

This may be used to estimate the rate at which the filter is being consumed or when the filter should be changed.

In a further embodiment of the invention, the change indicator as applied to exposure protection equipment could additionally use a pyroelectric or piezoelectric element/reagent combination to indicate when the target substance has broken through the filter or has saturated the filter. Thus, the pyroelectric or piezoelectric element and reagent device is installed in the space confined by the protective equipment (i.e., internal protected environment) or in the filter media container prior to adding the filter media. It should be noted that in this embodiment, the pyroelectric or piezoelectric element does not require that the filter be housed in a clear container or that any portion of the filter container is transparent. The reagent changes when exposed to the target substance. When the LED lights are flashed adjacent the pyroelectric or piezoelectric element, for example, the change in the reagent exposed to the target substance causes the film to generate an electrical signal proportionate to the concentration of the target substance. The piezo electric device may provide a digital display of the concentrations of the target substance giving a semi-quantitative or a qualitative indication of the target substance. The piezoelectric change indicator may initiate a visual, audible, or tactile alarm. Further, it may close or open a contact, trigger a system shutdown or startup, or stop the machine before the target substance breaks through the filter. The change indicator may further indicate the temperature and/or humidity (or water content) of the space contained by the protective equipment or the temperature and/or humidity (or water content) of the protective equipment filter material. In further embodiments, the change indicator includes indicators in glass tubes or other clear containers, and may be used in front of sensors such as PID's, FID's, and SAW.

In yet another embodiment of the invention, a breach detector/indicator system comprises at least two portions. One portion is situated in or adjacent the disposable respirator, canister, or cartridge. This portion is disposed with the consumed or used canister or cartridge. The second portion of the system is installed in the respirator face piece (i.e., externally of the filter) and is used with both the original and the replacement respirator cartridges. Further, wires and cables connecting the respirator to the control unit are situated in the interior of the mask.

In this embodiment, the first portion of the system incorporates a pyroelectric or piezoelectric element and reagent on the surface (see previous description and reference to published patent documents). A length of fiberoptic cable or light bar is attached to one side of the film (or both sides of the film) in the approximate location of the reagent. A wire connected to the pyroelectric or piezoelectric element carries the electronic signal when the film is twisted from the piezoelectric film to a control unit housed in a respirator mask or in the space confined by the protective equipment. The wire connection from the piezoelectric film in the filter material and the fiber optic cable to the control unit is made so as to be easily disconnected from the mask-installed or protective equipment installed control unit. The fiberoptic cable connection and the wire connection is preferably waterproof.

The pyroelectric or piezoelectric element, fiberoptic cable, and wire embedded in the media of the respirator cartridge extend through the filter media to the exterior of the cartridge and into the area inside the respirator mask. Inside the respirator mask, the fiberoptic cable and the wire connect to the control unit. The fiberoptic cable and the electrical wire run through the length of the cartridge and through the mask.

The wire and fiberoptic cable provide the connection to control units installed within the respirator mask. The control units may include the following elements:

LED, laser diode or other light source;

Battery (lithium or rechargeable);

Clock type device that instrumentally causes the light source to flash and establishes the start time and elapsed time;

A device to read the electrical output of the pyroelectric or piezoelectric element when the target substance breaks through the filter media and to recognize when the electrical output exceeds a prespecified level or levels (a set point) and trigger an alarm(s);

Audio alarm, or visual flashing alarm such as a flashing LED in front of the wearer's eye, or vibrating alarm on the wearer's face or head.

This system incorporates what may be termed as an "end of service life indicator (ESLI)." One variation of the ESLI includes a fiberoptic table that is removed from its sheathing at an end connected to the pyroelectric or piezoelectric element. The ends of the fiberoptic cable are preferably in a cannula, and well polished To obtain maximum light transmission, it is important that no optics are placed on the cable ends. Typically, the light is configured so as to flash as soon as the unit is hooked up. The basic response in a typical application will be a green light, which means that the connection of the fiberoptic cable is intact. In another mode, the indicator flashes a red light to reflect that the battery is good, that the cartridge has not experienced a break but the cartridge is consumed. This is a prompt for the user to change the cartridge. In yet another mode, the detector does not flash red or green, this reflects that the connection is broken or that the battery is dead.

The detector device according to the invention may have the ability to be "go," "no go," with one set point or may be able to indicate to the user when one or more percentages of the cartridges are consumed. This may be accomplished in two different methods. In one method, different signal outputs of the piezoelectric film or other change indicator are utilized. This is accomplished by different detectable ranges of different spots on the pyroelectric or piezoelectric element change indicator, with one spot being more sensitive than the other. Alternatively, this may be accomplished by locating the detection spots at different locations (depths) in the filter media. In this way, when one spot generates an output, the other spot has yet to be exposed. The position of the spot dictates the percentage of the filter remaining.

In yet a further variation of the breach detector/indicator system according to the invention, the first portion of the system utilizes a first fiber optic cable and a second fiber optic cable. The first fiber optic cable includes an end or tip whereon reagent is painted. This end is inserted into the respirator cartridge or filter media. The second fiber optic cable (or a split fiber optic cable) is provided for carrying the color back to the photocell or other optical sensor in the mask and connects to the control unit installed therein. Again, this connection is made so as to be easily connected or disconnected.

Preferably, the "reagent tip" of the fiber optic cable is buried to a depth in the filter media of the cartridge. This depth is such that it provides the percentage of remaining filter life desired. The opposite end or tip of the fiber optic cable extends into the respirator mask.

The second fiber optic cable which is connected to the control unit, may include the following elements:

An LED, laser die, or light source;

A battery (lithium or NiCad rechargeable);

A clock type device to intermittently cause a light source to flash;

A photocell or other optical sensor such as a photometer to read the light output reflected from the tip of the fiber optic cable. This photocell or other optical sensor may be used to read a single or multiple set points or levels, and trigger an alarm. Also, it can be used to measure various levels and trigger alarms at different locations of the filter media and or when a predetermined amount of the filet media is remaining or when a predetermined amount of time is remaining prior to the filter or exposure protection equipment breakthrough or failure; and Audio alarm, or visual flashing alarm such as flashing LED in front of the wearer's eye, or vibrating alarm on the wearer's face or head.

In yet another variation of the above system, the system is modified so as to be "passive." In this passive system, there is no photocell to read the change in color (or darkness density), and there are no audio, visual, or vibrating alarms. Such a system includes an LED, laser diode or other light source mechanism and a battery.

The LED transmits light through the fiberoptics to the reagent tip. The reflected light is then displayed in the mask. The reflected light would be observed by the user in an identical manner as described above. There is a color change, but the color change is displayed in the mask at the end of the fiberoptics. It may also be advantageous to use one strand (bundle) of fiberoptic cables to transmit the light to the reagent. Another strand is provided to carry the reflected light back to the mask (so as to be observable to the user). A bundle of strands may be used (if one strand is not thick enough), as well as an optical lens for magnifying the light. In either case, the reflected light or indication may be made more easily observable.

Several advantages are provided with this alternative embodiment. First, the color change or indication may be directed immediately in front of the wearer's eye in a full-facemask. Second, no penetration of the canister or changing of the canister or cartridge mold is required. Third, if the canister is hidden and cannot be seen, the fiber optic cable overcomes this problem by allowing the color change/indication to be observed at a different location.

In yet another embodiment of the invention, a powered air purifying respirator (PAPR) is provided utilizing a change indicator, according to the invention. The inventive respirator incorporates most of the preferred characteristics of the filter change indicator as described above. In these applications, the change indicator is used to indicate the proper time to change a filter. The inventive respirator may be used with the hood, helmet, or a respirator with a full or half mask.

In one application, the condition of the filter for the respirator is monitored using the color change indicator. Such a change indicator is preferably mounted in a clear filter container. In the alternative, the change indicator is positioned so that it is visible through a clear window of the filter container. In this way, the change indicator may be monitored from a short distance or externally in the protected environment. In one embodiment, the color change indicator RN 216 is located outside of the filter cartridge, preferably in the hood helmet area RN 820 or respirator mask areas RN 800 (see, e.g., FIG. 8 and FIG. 9A-C). In this way, the person using the respirator is made aware of any breakthrough of the target substance. In the alternative, the change indicator may be set at a much higher sensitivity so as to indicate a small amount of substance permeating the filter. Again, such an indication would notice the necessity for a filter change. Indicator RN 214 indicates breakthrough of the respirator cartridge and indicator RN 216 indicates leaks due to improper fitting of the face piece (FIG. 8 and FIG. 9A-B). Indicators RN 214 and RN 216 are positioned on the sight view of the user, in this manner the user can easily observe the indicators status. The positions of indicators RN 214 and RN 216 further allow surrounding observers to observe the status of the indicators.

An additional change indicator may be located on the exterior of the filter, in front of the filter media or in front of the respirator. The placement of the indicators and its sensitivity setting preferably indicate concentrations of the target substance in the protected environment. According to current NIOSHA requirements, powered air purifying respirators may be used only when the target substance is detected at a concentration 50 times the acceptable exposure limit (AEL) for the target chemical. PAPR's can be used only in environments in which the level of exposure to the chemical agent can be measured, and it must be detected in the appropriate levels. This is particularly important for use of PAPR's by medical staff during decontamination and treatment exercises (e.g., after a chemical biological incident).

In further embodiments, a piezoelectric element and reagent device may be placed in the filter in lieu of the color change indicator. In a further variation of the inventive PAPR, the change indicator (or piezoelectric device) may be equipped with a series of color change indicators or reagent spots (on the piezoelectric element). This allows the user to estimate the rate of filter breakthrough (as indicated by the rate of indication).

It should be noted that, in the application wherein a piezoelectric element reagent device is used, a pump may not be required for drawing air over the piezoelectric reagent separation filters. In these cases, the air fill from the pump in the PAPR may provide this function.

Referring to FIGS. 6 and 7, the color change indicator or piezo electric change indicator, according to the invention, may be used as a protective equipment chemical suit change indicator and chemical leak detector. In these applications, the change indicator may be used in fit testing the protective equipment chemical suit, or as an active alarm indicating the presence of leaks or suit failure while the protective equipment chemical suit is in service. In other applications, the change indicator is used to test the protective equipment chemical suits against the required standard, such as the time for solvents to break through the suit (e.g., solvents such as acetone, methanol, trichloral ethylene, kolulene, and other solvents). The change indicator may also be used to measure the temperature and humidity in the suit and to indicate heat stress.

In yet another application, the color change indicator is used to measure the quality of breathing air in the suit. This measurement is done by measuring the percent oxygen, carbon dioxide, carbon monoxide, oil mist, and other gases in the compressed breathing air. Preferably, the suit 601 is equipped with a clear window 611 or 612 through which the color change indicator is visible. The back of the color indicator is attached to the window and the opposite side faces the body of the person wearing the suit. The color indicator may be constructed in the suit in the same manner as the color indicator with the glove as described above. The change indicator may also be located at one location in the suit or several locations, such as the head, thorax, and lower leg areas (as shown in FIGS. 6 and 7). Such placements would tend to ensure a color change regardless of the properties of the target substance and its vapor pressure. For instance, two change indicators may be located at each location in the suit (see FIG. 7). One indicator would monitor the background and the other would indicate a leak or change. The color change indicator may be placed on the face shield of the chemical suit or the hood or helmet (see, e.g., FIG. 6B). In this way, both the wearer (inside the chemical suit) and an observer other than the wearer can see the same color change.

As before, the piezoelectric device may be used in place of the color change indicator, as shown in the chemical suite FIG. 6B. The piezoelectric device RN 714 connected to processor RN 750 preferably provides audio RN 770, visual RN 780, and vibrating RN 776 alarms (see, e.g., FIG. 6A). It may also provide the ability to trigger a radio for cell phone transmission RN 790 in the event of a leak or suit failure.

In yet another application, a change indicator according to the invention is used with an absorption tube that includes tubes of charcoal, silica, or other absorption material. The inventive absorption tube is provided with a clear window (or is entirely transparent). The back of the color change indicator is preferably positioned against the clear sides of the absorption tube, such that the indicator indicates when the tube is saturated or when the tube collects a target substance (before the sample is sent to the lab for testing). The color change indicator according to the invention may also be adapted for monitoring temperature and humidity. This is especially advantageous in situations wherein high temperature and/or humidity is known to cause a decrease in absorption capacity of the activated charcoal.

In yet another application, a color change indicator or piezoelectric change indicator according to the invention is used with oxygen concentrators, nitrogen concentrators, re-breathers, and other devices that push or pull fluids through a sieve material. Such sieve materials, e.g., zeolite, function to allow one or more chemicals to permeate the sieve while blocking or excluding other chemicals. Such technology is typically used in oxygen concentrators, and re-breathers used in extended underwater diving and rescue work. Typically, the sieves are generally circular containers with a large surface area and a limited depth. A container for the sieve material, in accordance with the invention, would include a clear window (or be entirely transparent) so as to allow the color change indicator to be observed from the outside, as previously described.

In addition to measuring the concentrations of both the contaminant gas (i.e., $CO2$) and the desired gas ($O2$), the inventive indicator is adapted to measure temperature and/or humidity. In these applications, high temperature and high humidity present certain problems with the operating efficiency of gas concentrators and re-breathers.

The inventive indicator produces a color change that indicates when the sieve should be changed or additional $O2$ added to the system, or $O2$ vented. In an application where the piezoelectric film device is used, automatic alarms and even valve controls may be incorporated. The inventive change indicator may also function to signal when the $O2$ compressed air supply is near depletion. For example, such an indication may be triggered upon comparison of the readings of the expiration of the sieve and the quality of the air supply (or the quality of the additional air being added).

In another embodiment of the invention, one or more colorimetric change indicators and/or piezoelectric and/or pyroelectric elements and/or other sensors and/or any combination of two or more calorimetric change indicators and/or pyroelectric and/or piezoelectric elements and/or other sensors capable of qualitatively indicating the presence and/or concentration and/or rate of change of one or more target substances including but not limited to oxygen and/or relative humidity and/or temperature and/or other target substances are located at and/or on the exterior of a respirator canister and/or cartridge and/or filter immediately in front of a respirator canister or cartridge filter intake and/or on the respirator canister or cartridge body for the purpose of acting as an end of service life indicator and/or for the purpose of collecting respirator canister and/or cartridge exposure to the target substance and/or oxygen and/or relative humidity in order to improve the accuracy and safety of the respirator change out schedule.

The concept is that the respirator change out schedule and/or the respirator canister or cartridge service life is based upon a manufacturer specified and/or recommended and/or estimated contaminant and target substance exposure capacity and/or estimated environmental conditions present during the use of the respirator canister or cartridge such as temperature, relative humidity, pressure, and altitude. The service life is based upon these estimates and to the extent that the respirator canister or cartridge is exposed to different concentrations of the target substance and/or different concentrations of the target substance for different periods of time and/or exposure duration than were estimated or used by the manufacturer to establish the respirator service life. The actual respirator service life will be greater than or less than the estimated respirator service life provided by the manufacturer. In the embodiment of this invention, the colorimetric and/or pyroelectric and/or piezoelectric and/or other sensor (including but not limited to electrochemical sensor, optical sensor, oxygen sensor, air flow sensor, catalytic bead or thermo sensor, chemfet sensor, chemiresistor sensor, solid state sensor, metal oxide sensor, photo ionization sensor, infrared sensor, surface acoustic wave sensor, impedence sensor, resistance sensor, acoustic infrared sensor, wave guide sensor, biological sensor, photometer, chemical warfare agent sensor, spectrophotometer, densitometer, fiber optic sensor, mass sensor, and/or optical sensors based upon reflected light interrogates the environment and environmental conditions including the oxygen concentration, relative humidity, temperature, air flow rate through the respirator flow path and target substance concentration or the contaminant capacity and other factors affecting respirator cartridge or canister, target substance breakthrough, and/or respirator canister or cartridge service life continuously, intermittently, on demand, actively, and/or passively and allows the wearer or a control unit to predict the respirator service life and the end of service life of the respirator canister or cartridge filter, and the transformer based upon the actual exposure to the target substance, oxygen, relative humidity, temperature, and/or the rate of change in the target substance, oxygen, relative humidity, temperature, air flow, target substance filter or transformer capacity, altitude, pressure, and/or indicator or sensor shelf life. This embodiment of the invention also provides the wearer with greater protection by indicating changes in the concentration of oxygen present in the environment and by indicating if the environment is deficient or becoming deficient in oxygen. In some cases, the target substance that the respirator canister and/or cartridge are designed to trap localize, absorb, adsorb, block or convert displaces the oxygen in the environment, resulting in a potentially dangerous oxygen deficient environment. The colorimetric change indicator or other sensor can indicate a qualitative, semi-quantitative, or quantitative change in the concentration of oxygen, as well as indicate a rate of change in the concentration of oxygen.

The pyroelectric and/or piezoelectric and/or other sensors can read the actual environmental conditions and/or predict the end of service life and/or the amount of respirator canister or cartridge filter material remaining or the time remaining prior to breakthrough and/or prior to the protective equipment or respirator cartridge or canister filter failure or protective equipment failure and/or prior to the end of service life and in conjunction with the sensor control unit and predetermined set points trigger alarms based upon desired safety considerations and actual environmental conditions.

The pyroelectric and/or piezoelectric sensor and/or other sensors mentioned above are not necessarily degraded by exposure to the target substance when the respirator canister or cartridge is not in use as long as the sensor control unit and sensor are turned off. However, the sensor and or indicator shall be suitable to be removed from the respirator cartridge or canister when the sensor or change indicator is not in use. The sensor and change indicator shall be covered and or stored in a cool dry place free of the target substance.

In this embodiment of the invention, the colorimetric change indicator, pyroelectric and piezoelectric element or other sensors are located on the exterior of or immediately in front of the respirator canister or cartridge intake and may be housed in a separate sensor assembly that can be temporarily or permanently attached, plugged into, snapped onto the respirator cartridge or canister assembly with screw threads or bayonet fitting and/or other means such that the sensors and/or control unit can be reused with different respirator canisters and/or cartridges.

The sensor assembly and/or the control unit shall consist of the energy source such as a battery, a memory device, a display, one or more alarms including audio visual and/or tactile alarms and associated electronics and/or optics and/or wiring.

The sensor control unit can display the sensor's total elapsed service life for the respirator cartridge or canister filter in seconds, minutes, hours, days, weeks, months, and/or years based upon (1) the elapsed service time, (2) the prior exposure to the target substance, (3) the environmental conditions and (4) the current rate of exposure and concentration of the target substance.

In this embodiment the contaminated fluid passes through filter material RN 420 in sorption-type cartridge RN 410 then circulates around the deflector in the detecting unit RN 440. Adjacent to the transparent or translucent wall RN 442 of the detection control unit RN 440 is the sensor 216 which is separated from the space into unit 410 by the chemical transformer 446 (if the transformation is necessary). When the optical properties of sensor 216 changes, it indicates the end of service life of the cartridge 410. The air flow passes additional sorption media in the reserve filter 460, which contain 20 to 25% sorbent volume, compare to cartridge 410, FIG. 10.

In another embodiment of this invention, the respirator canister or cartridge filter and the sensor and the control unit and the reserve respirator cartridge or canister filter shall be contained in three separate modules with common fillings. The sensor and the control unit shall be mounted in one module located after the respirator canister and cartridge filter and prior to the reserve respirator canister or cartridge filter. The sensor assembly and/or control unit may or may not be intrinsically safe or explosion proof.

This has the advantage of providing a standardized sensor assembly and control unit; there is no requirement to modify the respirator canister or cartridge. Different sizes of reserve filters can be provided to suit different target substances concentrations and/or other properties.

The control unit could record and display the cumulative time the sensors have been in use and/or that the respirator canister and/or cartridge has been in use as well as the estimated remaining life as specified by the manufacturer and as estimated based upon actual exposure conditions.

The embodiment of this invention may include or not include the use of transformers in front of the sensors. The invention teaches a method for improving the sensitivity, selectivity, and accuracy of detecting and/or measuring respirator cartridge or canister service life, predicting the end of service life, predicting the time before breakthrough and/or end of service life.

In another embodiment of the invention, a calorimetric change indicator for one or more chemical warfare agents and/or biological warfare agents is located on the exterior of the respirator canister or cartridge to act as an all clear indicator. The invention may incorporate one or more reagents to indicate the presence of one or more chemical warfare agents such as nerve agents, blister agents, blood agents, and choking agents, individually or simultaneously. The colorimetric device may require activation and may be used with or without a developer and/or pump to improve sensitivity, selectivity and/or speed of response and/or accuracy.

The colorimetric indicators have one or more reagent spots of various concentrations and may have an adhesive for attaching to the respirator canister or cartridge. The side of the colorimetric indicator exposed to the environment may be covered with an air and moisture impermeable material such as a metalyzed plastic film that is removed with each use of the canister or with each determination if the area is clear and it is safe to remove the respirator mask. The color change can be compared to the color of a comparator or calibration color spot to determine the concentration of the target substance and/or the concentration of the target substance may be read with an optical device such as a photometer, densitometer and/or spectrophotometer.

One embodiment of this invention can include the use of Acetyl cholinesterase enzyme for the detection of the presence and/or concentration of chemical warfare nerve agents such as organophosphate nerve agents. This reagent may also be used on or adjacent to a piezoelectric or pyroelectric element for detecting the presence and/or concentration of chemical warfare agents and for providing a digital display of the presence of the nerve agent or its concentration as well as triggering audible, visual, or tactile alarms.

Various embodiments of the present invention have been described herein. It should be understood by those of ordinary skill in the art, however, that the above described embodiments, are set forth merely by way of example and should not be interpreted as limiting the scope of the invention, which is defined by the appended claims. Other alternative embodiments, variations and modifications of the foregoing embodiments that embrace various aspects of the present invention will also be understood upon a reading of the detailed description in light of the prior art. For instance, it will be understood that application of a thermo strip or the various types and configurations of thermo strips, may be combined with features of other embodiments while many other features may be omitted or replaced.

What is claimed is:

1. A system for detecting a breach of an exposure protection device by an amount of a target substance, said system comprising:
    the exposure protection device that isolates a protected environment from an external environment potentially including a target substance, the device including a protective covering, the protective covering comprising at least one opening that is hermetically sealed by a substantially transparent window that protrudes outward from said exposure protection device; and
    a detector for indicating the presence of a predetermined level of the target substance, the detector being capable of producing visually observable indication upon detection of the level of target substance;
    wherein said detector is positioned within the protected environment in the vicinity of said window, such that the visually observable indication is observable from the external environment.

2. The system of claim 1, wherein said window is a transparent bubble container.

3. A system for detecting breach of properties of protective equipment, comprising:
    an exposure protection device that isolates a protected environment, the exposure protection device comprising:
        a protective covering comprising a first material;
        at least one opening; and
        a enclosure surrounding each opening, each enclosure comprising a transparent window hermetically sealed to a surface of the exposure protection device around each of the opening, wherein an inner environment of each enclosure is in communication with the protected environment and the transparent window consists of a second material that is more transparent than the first material and protrudes outward from said exposure protection device; and
        a detector element within at least one enclosure.

4. The system of claim 3, wherein the detector element indicates a presence of a target substance by changing an optical property.

5. The system of claim 3, wherein the detector element is a colorimetric detector element.

6. The system of claim 5, wherein the colorimetric detector element comprises a reactive reagent impregnated on a chemically inert flat transparent material.

7. The system of claim 5, wherein the colorimetric detector element comprises a layer of bonded particulates impregnated with a reactive reagent.

8. The system of claim 5, colorimetric detector element is visible from an external environment through the window.

9. The system of claim 3, wherein the detector element comprises bulk particulates impregnated with reactive reagent packed in a small cylindrical column and porous retainers.

10. The system of claim 3, comprising a stem, wherein the stem extends downwardly from the lens.

11. The system of claim 3, comprising a stem, wherein the stem extends downwardly from the lens to cover a portion of the detector element.

12. The system of claim 11, wherein the stem prevents exposure of a portion of the detector element to the target substance thus providing an unexposed area of the detector element to compare to the exposed portion of the detector element.

13. The system of claim 3, wherein the plurality of openings are located in exposure protective device at a location selected from the group consisting of a hand location, a face location, a chest location, a waist location, a knee location, a foot location and combinations thereof.

14. The system of claim 3, wherein the exposure protection device is a body suit, hood, glove, or a respiratory facemask.

15. The system of claim 5, wherein the colorimetric detector element is capable of indicating the presence of the target chemical by change of an optical property of the colorimetric detector element.

16. The system of claim 15, wherein the optical property is at least one property selected from color, hue, density, saturation, fluorescence, or luminescence.

17. The system of claim 3, wherein the window is flat, domed, prismatic, or cylindrical.

18. The system of claim 17, wherein the window is domed.

19. The system of claim 17, wherein the window is prismatic; the detector element is flat; and the detector element is positioned on one side of the prismatic window.

20. The system of claim 3, wherein the target substance is a chemical, protein, spore, dust, biological material, metal, toxins from a fungus, a plant, or an organism, biological warfare agents, or chemical warfare agents.

21. A system for detecting a breach of an exposure protection device by an amount of a target substance, said system comprising:
- an exposure protection device that isolates a protected environment from an external environment potentially including a target substance, the device including an opaque protective covering, the protective covering comprising at least one opening that is hermetically sealed by a substantially transparent window that protrudes outward from said exposure protection device; and
- a detector for indicating the presence of a predetermined level of the target substance, the detector being capable of producing a visually observable color indication upon detection of the level of target substance, wherein said detector is positioned within the protected environment in the vicinity of said window.

22. A system for detecting a breach of an exposure protection device by an amount of a target substance, said system comprising:
- an exposure protection device that isolates a protected environment from an external environment potentially including a target substance, the device including a protective covering, the protective covering comprising at least one opening that is hermetically sealed by a substantially transparent window, wherein the transparent window is more transparent than the protective covering and protrudes outward from said exposure protection device; and
- a detector for indicating the presence of a predetermined level of the target substance, the detector being capable of producing a visually observable color indication upon detection of the level of target substance, wherein said detector is positioned within the protected environment in the vicinity of said window.

* * * * *